(12) United States Patent
Iketani et al.

(10) Patent No.: US 8,233,038 B2
(45) Date of Patent: Jul. 31, 2012

(54) IMAGE-SIGNAL PROCESSING UNIT

(75) Inventors: Kohei Iketani, Saitama (JP); Go Matsui, Saitama (JP)

(73) Assignee: Hoya Corporation, Tokyo (JP)

( * ) Notice: Subject to any disclaimer, the term of this patent is extended or adjusted under 35 U.S.C. 154(b) by 1227 days.

(21) Appl. No.: 12/017,406

(22) Filed: Jan. 22, 2008

(65) Prior Publication Data

US 2008/0174701 A1    Jul. 24, 2008

(30) Foreign Application Priority Data

Jan. 23, 2007 (JP) ................. 2007-013038

(51) Int. Cl.
*A62B 1/04* (2006.01)

(52) U.S. Cl. .......... 348/65; 348/441; 348/453; 348/659; 348/660; 348/661; 348/266; 348/273; 348/448; 348/450

(58) Field of Classification Search .............. 348/65, 348/266, 273, 441, 448, 450, 453, 659, 660, 348/661
See application file for complete search history.

(56) References Cited

U.S. PATENT DOCUMENTS

| | | | | |
|---|---|---|---|---|
| 5,621,465 A | * | 4/1997 | Kondo | 375/240.01 |
| 5,786,872 A | * | 7/1998 | Miyazaki et al. | 348/669 |
| 5,812,187 A | * | 9/1998 | Watanabe | 348/70 |
| 6,297,855 B1 | * | 10/2001 | Kondo et al. | 348/663 |
| 7,077,804 B2 | * | 7/2006 | Ota | 600/180 |
| 7,420,623 B2 | * | 9/2008 | Nakakuki | 348/625 |
| 7,847,805 B2 | * | 12/2010 | Ogasawara et al. | 345/593 |
| 2002/0110274 A1 | * | 8/2002 | Yamamoto | 382/154 |

FOREIGN PATENT DOCUMENTS

JP    11-136693    5/1999

* cited by examiner

*Primary Examiner* — Yasin Barqadle
*Assistant Examiner* — Van Kim T Nguyen
(74) *Attorney, Agent, or Firm* — Greenblum & Bernstein, P.L.C.

(57) ABSTRACT

An image-signal processing unit comprising a first and second luminance calculation block, a correction-value calculation block, and a subtraction block, is provided. The first luminance calculation block calculates a first luminance corresponding to the sum of a plurality of primary color light components. Each of them is multiplied by a coefficient from a first coefficient combination. The second luminance calculation block calculates a second luminance corresponding to the sum of a plurality of the primary color light components. Each of them is multiplied by a coefficient from a second coefficient combination. The correction-value calculation block calculates a luminance correction value according to the second luminance if the first luminance is greater than a threshold value. The subtraction block calculates a corrected luminance by subtracting the luminance correction value from the first luminance.

20 Claims, 14 Drawing Sheets

IMAGE-SIGNAL PROCESSING UNIT

BACKGROUND OF THE INVENTION

1. Field of the Invention

The present invention relates to an image-signal processing unit that carries out signal processing on an image signal generated by capturing an optical image in which the amount of a specific primary color is far greater than the other primary colors, such as in an optical image captured by an electronic endoscope.

2. Description of the Related Art

An imaging device generates an image signal corresponding to a captured optical image of a subject. Predetermined signal processing is carried out on the generated image signal so that the colors in a subject image are displayed as accurately as possible. After the image signal undergoes predetermined signal processing, the rendered image is displayed on a monitor.

Imaging devices may be mounted in various apparatuses. For example, an electronic endoscope which comprises an imaging device at the head end of an insertion tube is known. A medical electronic endoscope is used to observe the inside of the human body. CCD imaging devices with complementary color filters are generally used in such medical electronic endoscopes.

A CCD imaging device with complementary color filters generates complementary-color signal components, such as Mg, Ye, G, and Cy. In the signal processing for a general medical electronic endoscope, a wide-band luminance signal and a narrow-band luminance signal are generated based on the complementary color signal. In addition, chrominance difference signals are generated based on the narrow-band luminance signal. The wide-band luminance signal and the chrominance difference signals are transmitted to a monitor. The monitor generates primary color signal components, such as R, G, and B, based on the received wide-band luminance signal and the chrominance difference signals. An image based on the primary color signal components is displayed on the monitor. Incidentally, the primary color signal components can be generated in the endoscope processor and transmitted to the monitor.

The main subject of a medical electronic endoscope is the inside of an organ, whose optical image is mostly reddish. When a reddish optical image is captured, it is possible for the signal level of just the red signal component (which is generated based on the wide-band luminance signal) to exceed the upper limits of the endoscope processor or a monitor. If the signal level of only the red signal component exceeds the upper limit, colors cannot be accurately displayed on a monitor.

SUMMARY OF THE INVENTION

Therefore, an object of the present invention is to provide an image-signal processing unit that carries out signal processing on image signals so that true colors can be displayed in an image based on the image signal even if the intensity of a specific color is much greater than the other colors in a captured optical image.

According to the present invention, an image-signal processing unit comprising a receiver, a first and second luminance calculation block, a comparison block, a correction-value calculation block, and a subtraction block, is provided. The receiver receives an image signal. The image signal comprises a plurality of pixel signal. The pixel signal is generated according to the amount of light received by a pixel. A plurality of the pixels are arranged on a light-receiving surface of an imaging device. The first luminance calculation block calculates a first luminance corresponding to the sum of a plurality of primary color light components. Each of them is multiplied by a coefficient from a first coefficient combination, for each of the pixels, based on the image signal. The second luminance calculation block calculates a second luminance corresponding to the sum of a plurality of the primary color light components multiplied by a coefficient from a second coefficient combination, for each of the pixels, based on the image signal. The ratio of the coefficient by which a first primary color light component is multiplied, to the coefficient by which a second primary color light component is multiplied, in the second coefficient combination is greater than the ratio in the first coefficient combination. The comparison block compares the first luminance with a threshold value. The correction-value calculation block calculates a luminance correction value according to the second luminance if the first luminance is greater than the threshold value. The subtraction block calculates a corrected luminance by subtracting the luminance correction value from the first luminance.

Further, the image-signal processing unit comprises a chrominance-difference calculation block and an output block. The chrominance-difference calculation block calculates a chrominance difference for each of the pixels based on the image signal. The output block outputs a chrominance difference signal and a luminance signal, corresponding to the chrominance difference and the corrected luminance, respectively, for each of the pixels, if the first luminance is greater than the threshold value. Or, the output block outputs a chrominance difference signal and a luminance signal, corresponding to the chrominance difference and the first luminance, respectively, for each of the pixels, if the first luminance is lower than the threshold value.

Further, the image-signal processing unit comprises a light-source determination block. The light-source determination block determines the kind of light source emitting illumination light for a subject. An optical image of the subject is captured by the imaging device. The second coefficient combination is modified according to the determination of the kind of light source made by the light-source determination block. The image-signal processing unit is mounted in an endoscope comprising the imaging device.

Further, the image-signal processing unit comprises an endoscope determination block. The endoscope determination block determines the kind of endoscope comprising the imaging device. The second coefficient combination is modified according to the determination of the kind of endoscope made by the endoscope determination block. The image-signal processing unit is mounted in an endoscope processor carrying out signal processing on the image signal.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
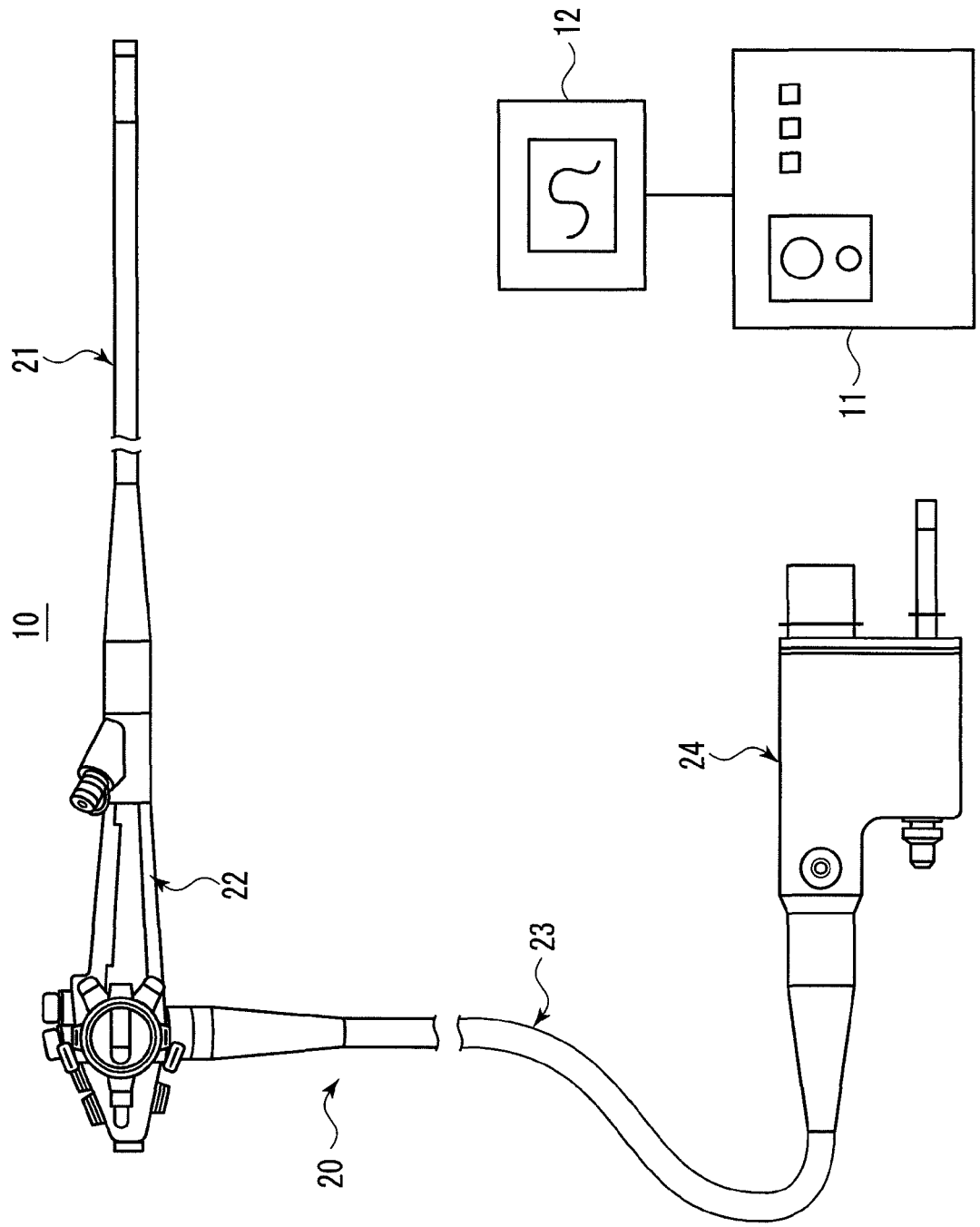
FIG. 1 is an outside view of an endoscope system having an image-signal processing unit as a first embodiment of the present invention.

The present invention is described below with reference to the first and second embodiments shown in the drawings.

In FIG. 1, an endoscope system 10 of the first embodiment comprises an electronic endoscope 20, an endoscope processor (image signal processor) 11, and a monitor 12. The endoscope processor 11 is connected to the electronic endoscope 20 and the monitor 12.

A part of the electronic endoscope 20 is inserted into the human body, for example. The electronic endoscope captures an image in the body. An image signal corresponding to the captured optical image is generated. The image signal is transmitted to the endoscope processor 11. The endoscope processor 11 carries out predetermined signal processing on the received image signal. The image signal, having undergone predetermined signal processing, is transmitted to the monitor 12, where an image corresponding to the image signal is displayed.

The electronic endoscope 20 comprises an insertion tube 21, a control block 22, a connection tube 23, and a connector 24. The base end of the insertion tube is connected to the control block 22. The control block 22 is connected to the connector 24 via the connection tube 23.

The insertion tube 21 is flexible, and may be inserted into a body cavity. The control block 22 has switches for initiating some functions of the electronic endoscope 20 and the endoscope system 10. The electronic endoscope 20 is connected to the endoscope processor 11 by inserting the connector 24 into the terminal (not depicted) of the endoscope processor 40.

Figure 2:
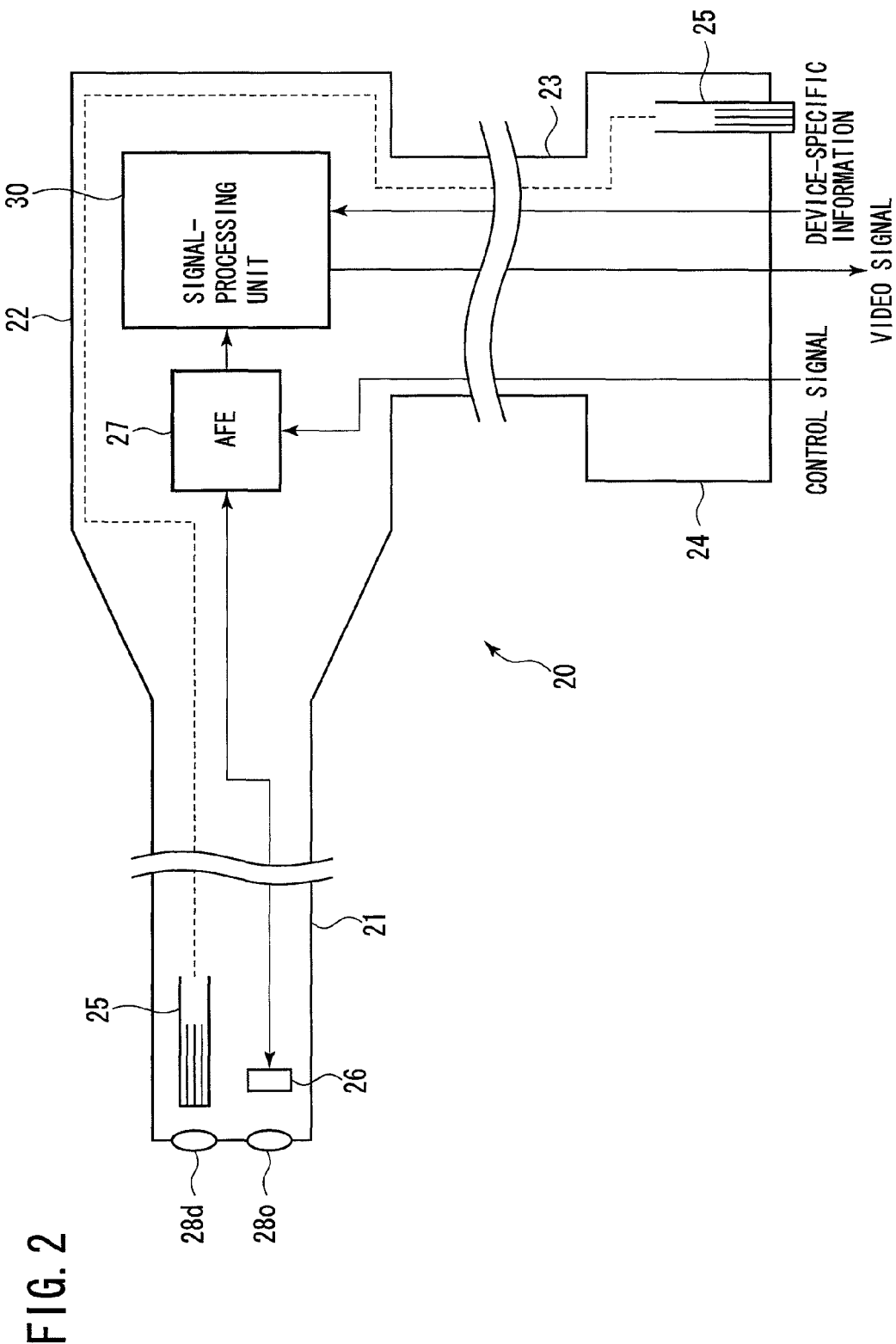
FIG. 2 is a block diagram showing the internal structure of the electronic endoscope of the first embodiment.

The internal structure of the electronic endoscope 20 is explained with reference to FIG. 2. The electronic endoscope 20 comprises a light guide 25, an imaging device 26, an analog front end (AFE) 27, a signal-processing unit (image-signal processing unit) 30, and other components.

The light guide 25 is a bundle of optical fibers, of which one end is mounted in the connector 24 and the other end is mounted at the head end of the insertion tube 21. The imaging device 26 is mounted at the head end of the insertion tube 21. The AFE 27 and the signal-processing unit 30 are mounted in the connector 24.

When the connector 24 is inserted into the terminal of the endoscope processor 11, the light guide 25 is optically connected to the light source (not depicted) mounted in the endoscope processor 11. Illumination light emitted by the light source is transmitted by the light guide 25. The illumination light transmitted to the exit end of the light guide 25 illuminates a peripheral area around the head end of the insertion tube 21 after passing through a diffuser lens 28$d$. Illumination light reflected from the subject is incident onto the light-receiving surface of the imaging device 26 after passing through an object lens 28$o$. The imaging device 26 is a CCD imaging device.

Figure 3:
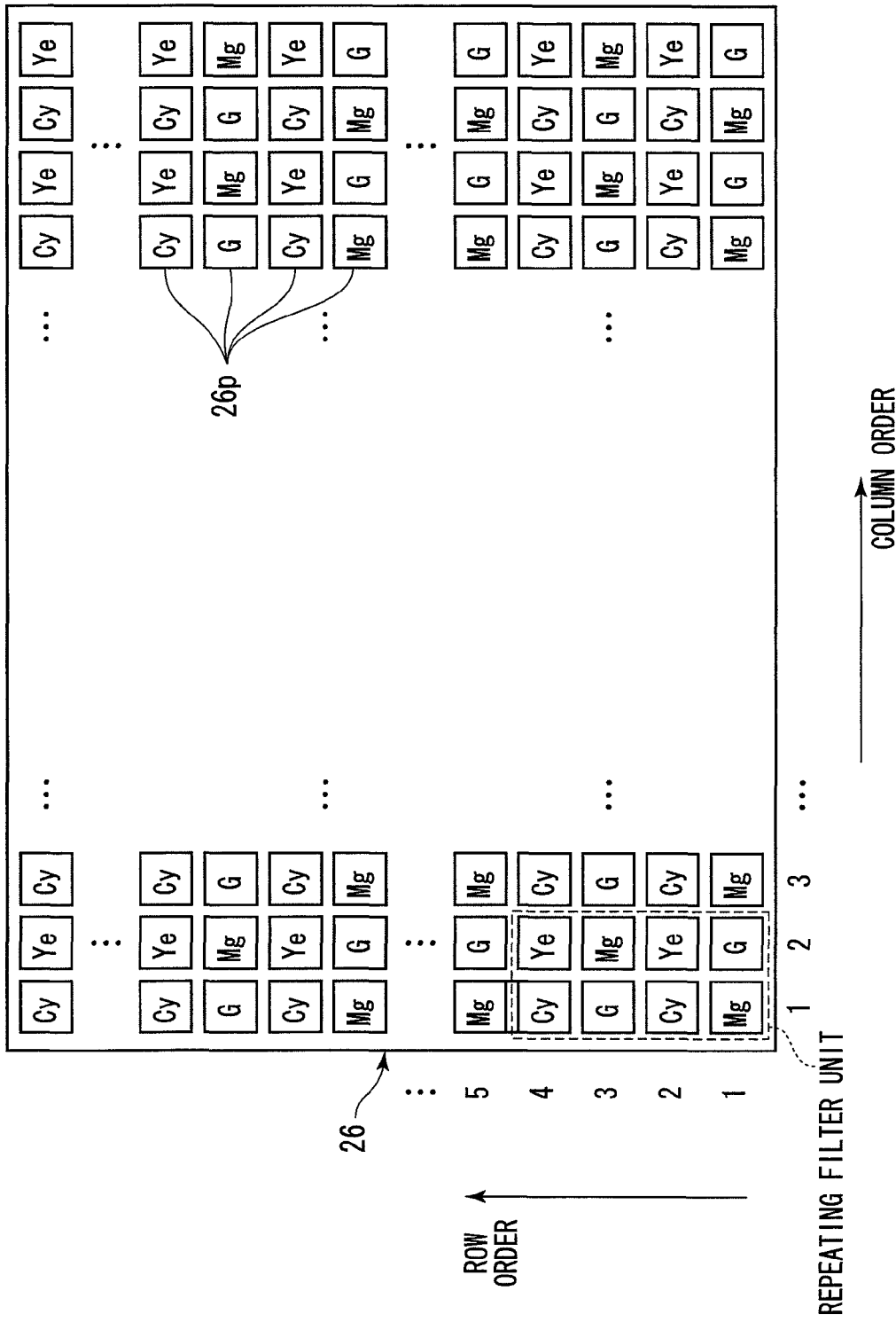
FIG. 3 shows an arrangement of complementary color filters on the light-receiving surface of the imaging device.

As shown in FIG. 3, A plurality of pixels 26$p$ are arranged in two dimensions on the light-receiving surface of the imaging device 26. In the explanation below, pixels are arranged in rows ordered from bottom to top, and in columns ordered from left to right. Each pixel 26$p$ is covered with color filters in the complementary-color-difference line-sequential arrangement. Accordingly, a repeating filter unit has two columns and four rows. The first column which comprises (from bottom to top) pixels covered with magenta, cyan, green, and cyan, and is flanked by a second column of pixels covered with green, yellow, magenta, and yellow.

Each pixel 26$p$ receives the color light component which passes through the color filter covering it. The pixel 26$p$ generates a pixel signal according to the amount of color light component it receives. Pixels covered with magenta, cyan, green, and yellow color filters generate pixel signals according to the color of their filters, hereinafter referred to as Mg, Cy, G, and Ye, (complementary color signal component).

The imaging device 26 is driven by the AFE 27 so that the imaging device 26 alternately and repeatedly outputs both even- and odd-field image signals every 1/60th second. The AFE 27 is controlled by a timing controller (not depicted) mounted in the endoscope processor 11.

In the even field, a pixel signal generated by a pixel 26$p$ located in an odd row is mixed with the pixel signal generated by a pixel 26$p$ located in the even row directly above it. The mixed pixel signals are output in row direction order. After outputting all mixed pixel signals generated in the odd row, mixing of the pixel signals and outputting of the mixed pixel signals commence in the next odd row.

For example, pixel signals generated by the pixels arranged in the first, third, . . . , (2n−1)st, and (2n+1)st rows are mixed with pixel signals generated by the pixels arranged in the second, fourth, . . . , 2 nth, and (2n+2)nd rows, respectively. Accordingly, in the first row, mixing of (Mg+Cy) and (G+Ye) repeats alternately starting from the left side. These mixed pixel signals are output in order. In the next odd row, that is the third row, mixing of (G+Cy) and (Mg+Ye) also repeats alternately starting from the left side. These mixed pixel signals are also output in order.

In the odd field, a pixel signal generated by a pixel 26$p$ located in an even row is mixed with the pixel signal generated by the pixel 26$p$ located in the odd row directly above it. The mixed pixel signals are output in row direction order.

After outputting all mixed pixel signals generated in the even row, mixing of the pixel signals and outputting of the mixed pixel signals commence in the next even row.

For example, pixel signals generated by the pixels 26p arranged in the second, fourth, . . . , 2 nth, and (2n+2)nd rows are mixed with pixel signals generated by the pixels 26p arranged in the third, fifth, . . . , (2n+1)st, and (2n+3)rd rows, respectively. Accordingly, in the second row, mixing of (Cy+G) and (Ye+Mg) repeats alternately starting from the left side. These mixed pixel signals are output in order. In the next even row, that is the fourth row, mixing of (Cy+Mg) and (Ye+G) also repeats alternately starting from the left side. These mixed pixel signals are output in order.

The even- and odd-field image signals comprise a plurality of mixed pixel signals output in the even and odd fields, respectively. The even- and odd-field image signals output from the imaging device 26 are transmitted to the AFE 27.

The AFE 27 comprises a correlated double sampling (CDS) circuit (not depicted) and an A/D converter (not depicted). The AFE 27 carries out correlated double sampling signal processing on the received image signal. In addition, the AFE 27 converts the analog image signal to a digital image signal.

The image signal is transmitted to the signal-processing unit 30. The signal-processing unit 30 carries out image-signal processing on the received image signal, as explained below.

Figure 4:
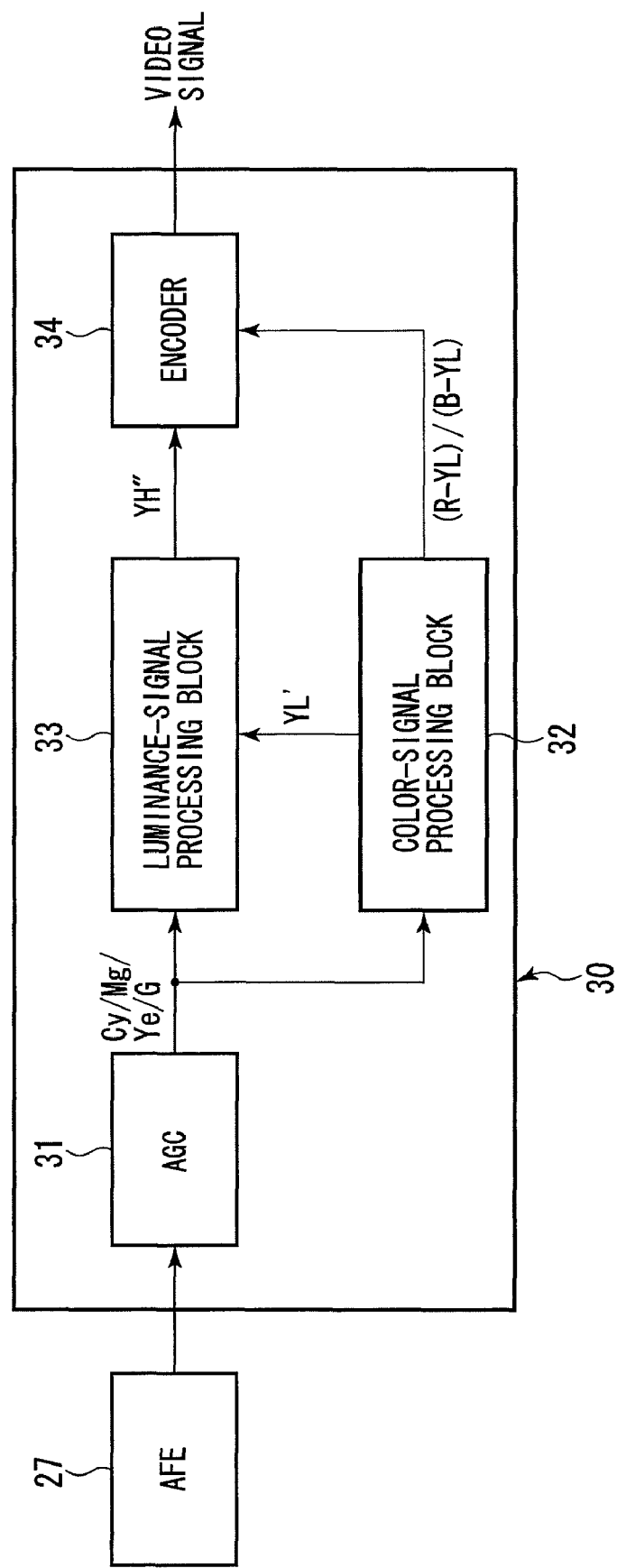
FIG. 4 is a block diagram showing the internal structure of the signal-processing unit of the first and second embodiments.

As shown in FIG. 4, the signal-processing unit 30 comprises an AGC (receiver) 31, a color-signal processing block 32, a luminance-signal processing block (luminance-signal correction block) 33, and an encoder (output block) 34.

The image signal which the signal-processing unit 30 receives is input to the AGC 31, which carries out a gain control on the received image signal. The AGC transmits the mixed pixel signals, (Mg+Cy), (Ye+G), (G+Cy), and (Mg+Ye), to the color-signal processing block 32 and the luminance-signal processing block 33.

The color-signal processing block 32 generates chrominance difference signals for red and blue, hereinafter referred to as R-YL and B-YL, and a second narrow-band luminance signal, hereinafter referred to as YL', for each pixel 26p based on the mixed pixels signals. The luminance-signal processing block 33 generates a corrected luminance signal, hereinafter referred to as YH", based on the mixed pixel signals and YL'.

The R-YL, B-YL, and YH" for all pixels 26p are transmitted to the encoder 34. The encoder 34 generates a video signal by encoding the R-YL, B-YL, and YH", and converting the digital signal into an analog signal. In addition, the encoder 34 transmits the video signal to the endoscope processor 11. Finally, the video signal is used for rendering an image on the monitor 12.

Figure 5:
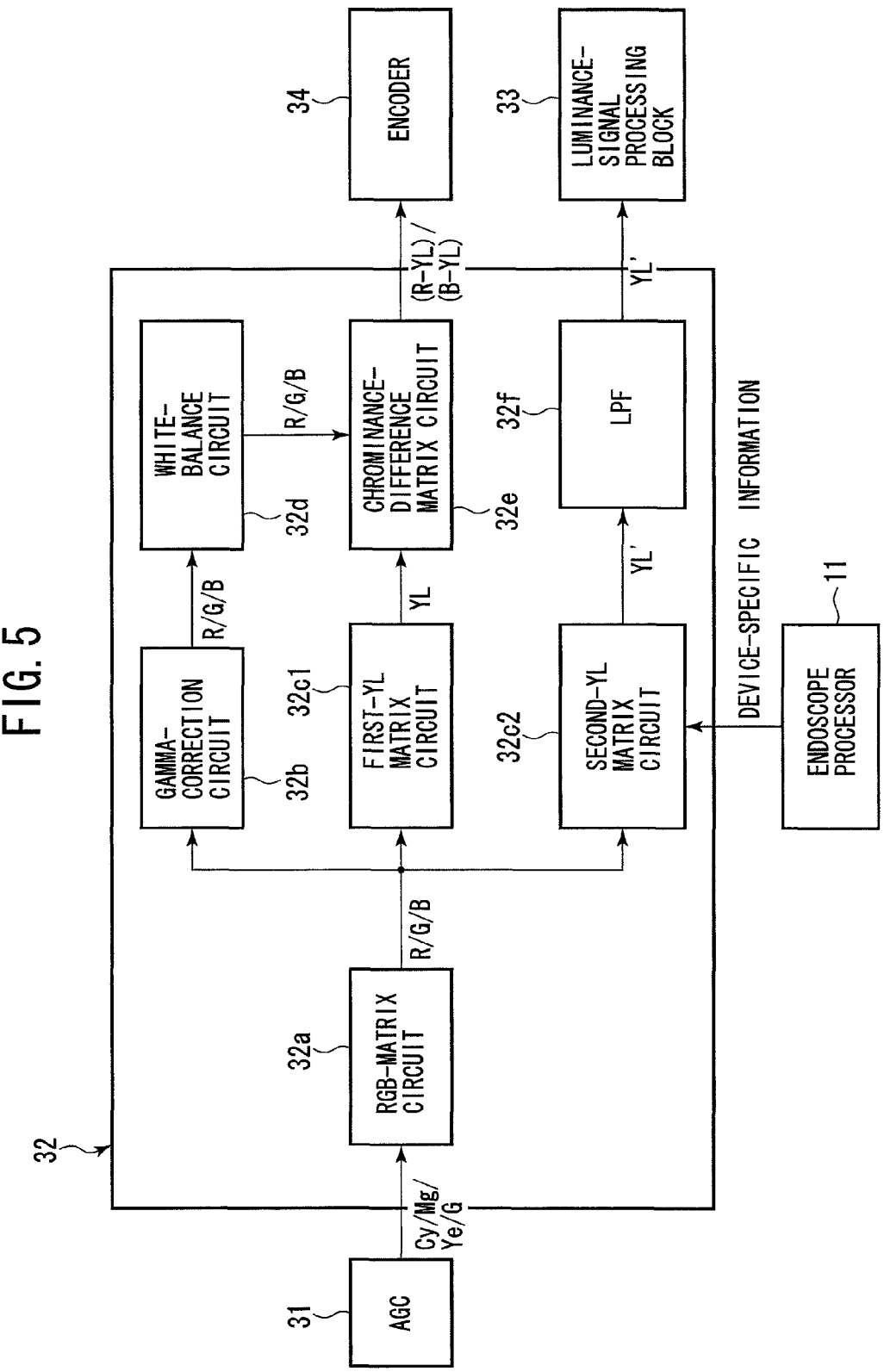
FIG. 5 is a block diagram showing the internal structure of the color-signal processing block in the first embodiment.

Next, the structure and function of the color-signal processing block 32 as it generates the R-YL and B-YL, is explained in detail below. As shown in FIG. 5, the color-signal processing block comprises an RGB-matrix circuit (primary-color signal generation block) 32a, a gamma-correction circuit 32b, first- and second-YL matrix circuits 32c1 and 32c2, a white-balance circuit 32d, a chrominance-difference matrix circuit (chrominance-difference calculation block) 32e, and an LPF (edge-enhancement block) 32f.

The image signal which the color-signal processing block 32 receives is input to the RGB-matrix circuit 32a. The RGB-matrix circuit 32a carries out RGB matrix processing on the received image signal. Through the RGB matrix processing, the primary color signal composed of red, green, and blue signal components (hereinafter referred to as R, G, and B) is generated from the Mg, Cy, Ye, and G. R, G, and B vary according to the amounts of the received red light component (second primary color light component), the received green light component (first primary color light component), and the received blue light component (primary color light component), respectively. The Mg, Cy, and Ye vary according to the amounts of received magenta, cyan, and yellow light components, respectively.

In the explanation below, a pixel from which R, G, and B are generated according to the RGB matrix processing is designated a focused pixel. The signals of certain pixels at predetermined locations around the focused pixel are associated with the focused pixel. The predetermined locations are the eight pixels within four rows and two columns including the focused pixel in the lower left corner.

For example, in the even field, if the pixel in the first row of the first column is regarded as the focused pixel, the signals of the pixels in the first, second, third, and fourth rows of the first and second columns correspond to the focused pixel (see FIG. 3). Incidentally, in the even field, the signals of the pixels in the first and second rows of the first column are output as a mixed pixel signal (Mg+Cy) of the pixel in the first row of the first column. Likewise, the signals of the pixels in the first and second rows of the second column are output as a mixed pixel signal (G+Ye) of the pixel in the first row of the second column. Similarly, the signals of the pixels in the third and fourth rows of the first column are output as a mixed pixel signal (G+Cy) of the pixel in the third row of the first column. Finally, the signals of the pixels in the third and fourth rows of the second column are output as a mixed pixel signal (Mg+Ye) of the pixel in the third row of the second column.

The same rule applies for the second column, such that the pixel signals of the first to fourth rows of the second and third columns correspond to a focused first row, second column pixel. Similarly, the pixel signals from the first and second rows of the second column are output as a mixed pixel signal (G+Ye) for that focused pixel. Similarly, the pixel signals from the pixels in the first and second rows of the third column are output as a mixed pixel signal (Mg+Cy) for that focused pixel. Similarly, the pixel signals from the pixels in the third and fourth rows of the second column are output as a mixed pixel signal (Mg+Ye) for that focused pixel. Finally, the pixel signals from the pixels in the third and fourth rows of the third column are output as a mixed pixel signal (G+Cy) for that focused pixel.

If a pixel in an odd row is regarded as the focused pixel in the even field, similar to the above, the four mixed pixel signals of the four pixels in the same location relative to the focused pixel (as described above) correspond to the focused pixel.

If a pixel in an even row is regarded as the focused pixel in the odd field, the four mixed pixel signals of the four pixels in the same location relative to the focused pixel (as described above) correspond to the focused pixel, similar to the case of the even field.

For a focused pixel in any location, the mixed pixel signals, (Mg+Cy), (G+Ye), (G+Cy), and (Mg+Ye) will be output in the even or odd field, and correspond to the focused pixel.

For RGB matrix processing on the focused pixel, the mixed pixel signals corresponding to the focused pixel are input to the RGB-matrix circuit 32a. The received mixed pixel signals are converted into R, G, and B components, according to equation (1) below. The generated R, G, and B components are transmitted from the RGB-matrix circuit 32a to the gamma-correction circuit 32b, and the first- and second-YL matrix circuit 32c1 and 32c2.

$$\begin{pmatrix} R \\ G \\ B \end{pmatrix} = \begin{pmatrix} R1 & R2 & R3 & R4 \\ G1 & G2 & G3 & G4 \\ B1 & B2 & B3 & B4 \end{pmatrix} \begin{pmatrix} G+Cy \\ Mg+Ye \\ Mg+Cy \\ G+Ye \end{pmatrix} \quad (1)$$

The gamma-correction circuit 32b carries out gamma correction processing on R, G, and B, separately. R, G, and B, having undergone gamma-correction processing, are transmitted to the white-balance circuit 32d. The white-balance circuit 32d carries out white-balance processing on R, G, and B, separately. R and B, having undergone white-balance processing, are transmitted to the chrominance-difference matrix circuit 32e.

The first-YL matrix circuit 32c1 receives R, G and B, as described above. The first-YL matrix circuit 32c1 generates the first narrow-band luminance signal, hereinafter referred to as YL, by summing up R, G, and B, after multiplication by the coefficients, 0.3, 0.59, and 0.11, respectively. YL is transmitted to the chrominance-difference matrix circuit 32e.

The chrominance-difference matrix circuit 32e receives R and B, after having undergone white-balance processing, and YL, as described above. The chrominance-difference matrix circuit 32e generates R-YL and B-YL based on R, B, and YL. R-YL and B-YL are transmitted to the encoder 34.

The second-YL matrix circuit (light-source determination block) 32c2 receives R, G, and B, as described above. The second-YL matrix circuit 32c2 generates the YL' by summing up R, G, and B. multiplied by coefficients predetermined according to device-specific information.

The device-specific information indicates the kind of light source (not depicted) mounted in the endoscope processor 11 and transmitted to the second-YL matrix circuit 32c2 when the electronic endoscope 20 is connected to the endoscope processor 11. A halogen lamp, a xenon lamp, or a metal halide lamp may be used as the light source of electronic endoscope 20.

The second-YL matrix circuit 32c2 comprises a memory (not depicted) which stores a table of coefficients for each primary-color signal component corresponding to the device-specific information. The second-YL matrix circuit 32c2 reads the coefficients to multiply R, G, and B according to the received device-specific information.

If the light source is a halogen lamp, YL' is calculated as YL'=0R+0.9G+0.1B. If the light source is a xenon lamp, YL' is as YL'=0.3R+0.5G+0.2B. If the light source is a metal halide lamp, YL' is calculated as YL'=0.3R+0.7G+0B.

Figure 6A:
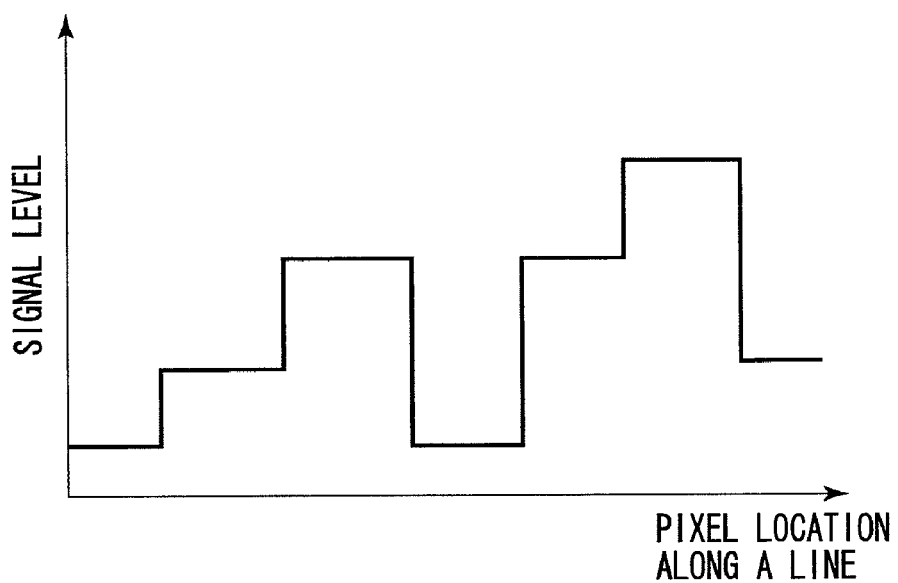
FIG. 6A is a graph showing the luminance signal levels of pixels arranged in line before removing the high frequency components.
Figure 6B:
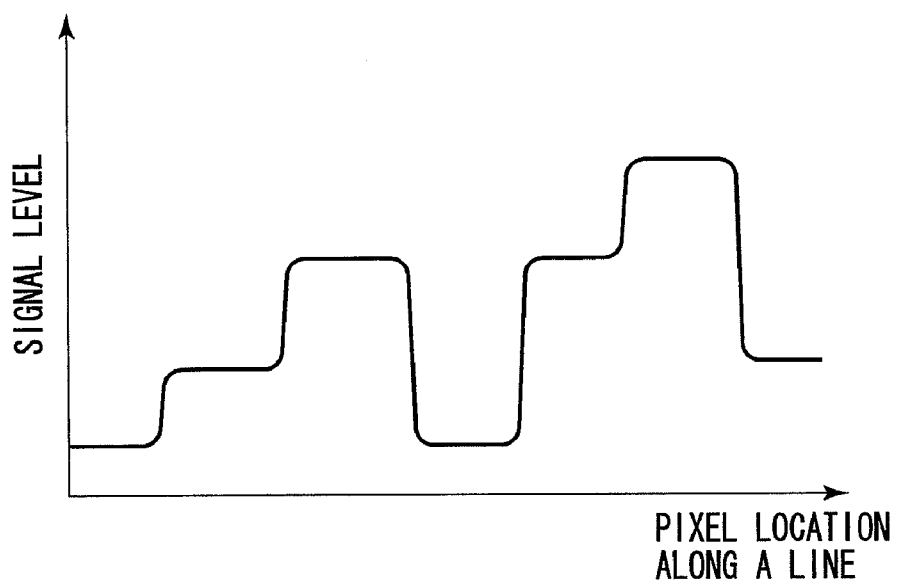
FIG. 6B is a graph showing the luminance signal levels of pixels arranged in line after removing the high frequency components.

The generated YL' is transmitted from the second-YL matrix circuit 32c2 to the LPF 32f. The LPF 32f removes the high frequency components from the spatial frequency represented by the YL's corresponding to the successively arranged pixels. For example, if the curve of signal levels of the YL's corresponding to the successively arranged pixels has a step shape (see FIG. 6A), the absolute value of rate of change in the curve is lowered by the LPF 32f (see FIG. 6B). YL', whose high frequency components have been removed, is transmitted to the luminance-signal processing block 33.

Figure 7:
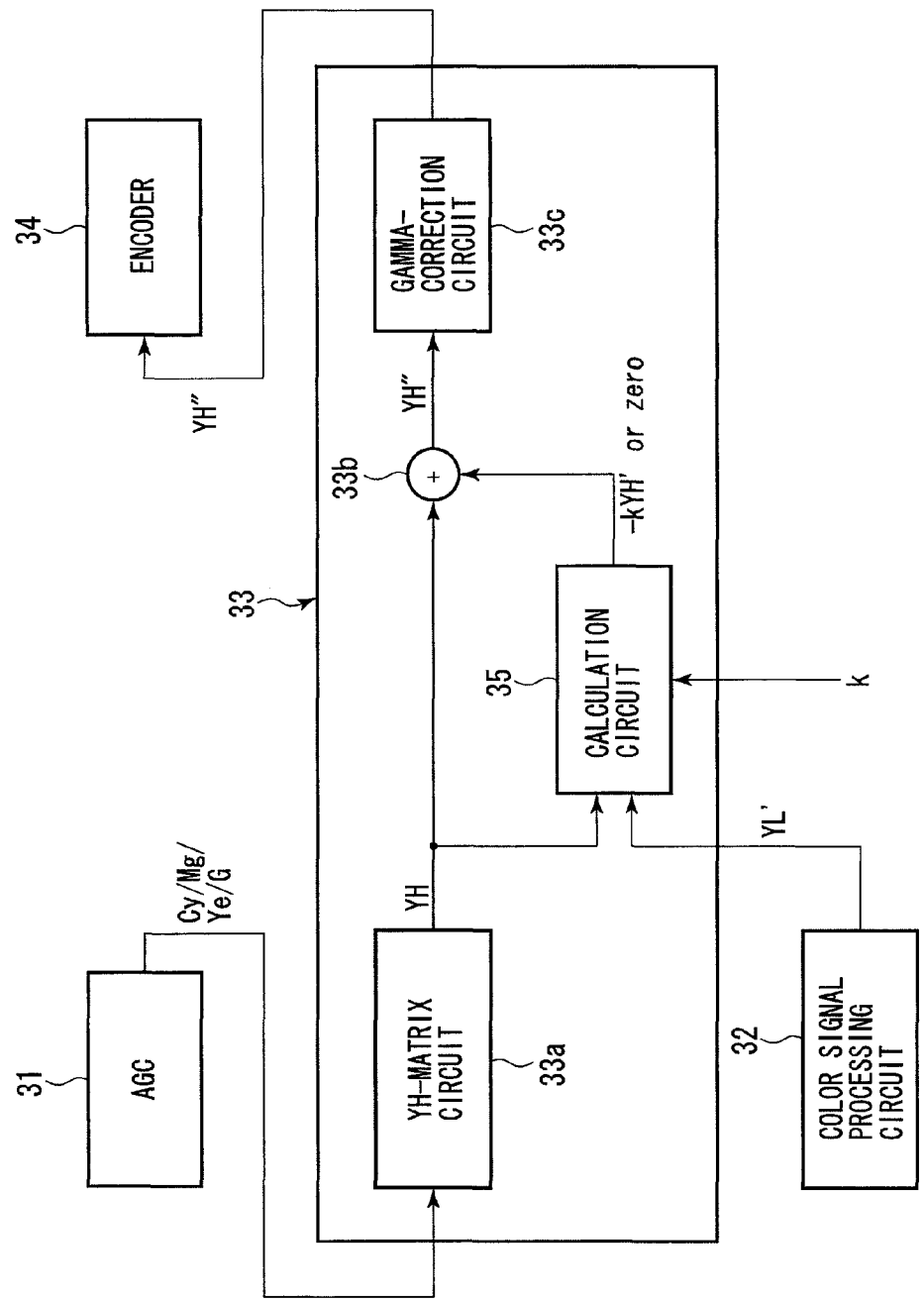
FIG. 7 is a block diagram showing the internal structure of the luminance-signal processing block in the first and second embodiments.

Next, the structure and the function of the luminance-signal processing block 33 as it generates YH" is explained in detail below. As shown in FIG. 7, the luminance-signal processing block 33 comprises a YH-matrix circuit (first luminance calculation circuit) 33a, a calculation circuit 35, an adder circuit (subtraction block) 33b, and a gamma-correction circuit 33c.

As described above, the luminance-signal processing block 33 receives the mixed pixel signals. The mixed pixel signal which the luminance-signal processing block 33 receives is input to the YH-matrix circuit 33a. The YH-matrix circuit 33a carries out YH matrix processing on the received mixed pixel signals. In YH matrix processing, the four mixed pixel signals for one pixel, (Mg+Cy), (Ye+G), (G+Cy), and (Mg+Ye) are summed and a first wide-band luminance signal (first luminance), hereinafter referred to as YH, is generated. The signal level of YH varies according to the brightness at the pixel 26p.

The signal levels of Mg, CY, and Ye are equivalent to the signal levels of (R+B), (G+B), and (R+G), respectively. Accordingly, the signal level of YH is equivalent to (2R+3G+2B). This means that YH is equivalent to the value calculated by summing the red, green, and blue light components multiplied by 2, 3, and 2 (the first coefficient combination), respectively. YH is transmitted from the YH-matrix circuit 33a to the calculation circuit 35 and the adder circuit 33b.

The calculation circuit 35 decides whether to calculate a correction signal, hereinafter referred to as kYH', based on the received YH. If the calculation circuit 35 decides to calculate kYH', as explained below, it calculates kYH' and outputs it to the adder circuit 33b after multiplying it by −1. If the calculation circuit 35 decides not to calculate kYH', it outputs a zero signal, (i.e. a signal level of zero), to the adder circuit 33b.

The adder circuit 33b generates YH" by adding up the YH from the YH-matrix circuit 33a and the −kYH' or the zero signal from the calculation circuit 35. Accordingly, if the calculation circuit 35 calculated kYH', YH" will equal (YH−kYH'). On the other hand, if the calculation circuit 35 did not calculate kYH', YH" will be YH.

YH" is transmitted from the adder circuit 33b to the gamma-correction circuit 33c. The gamma-correction circuit 33c carries out gamma correction processing on YH". YH", having undergone gamma correction processing, is transmitted to the encoder 34.

Figure 8:
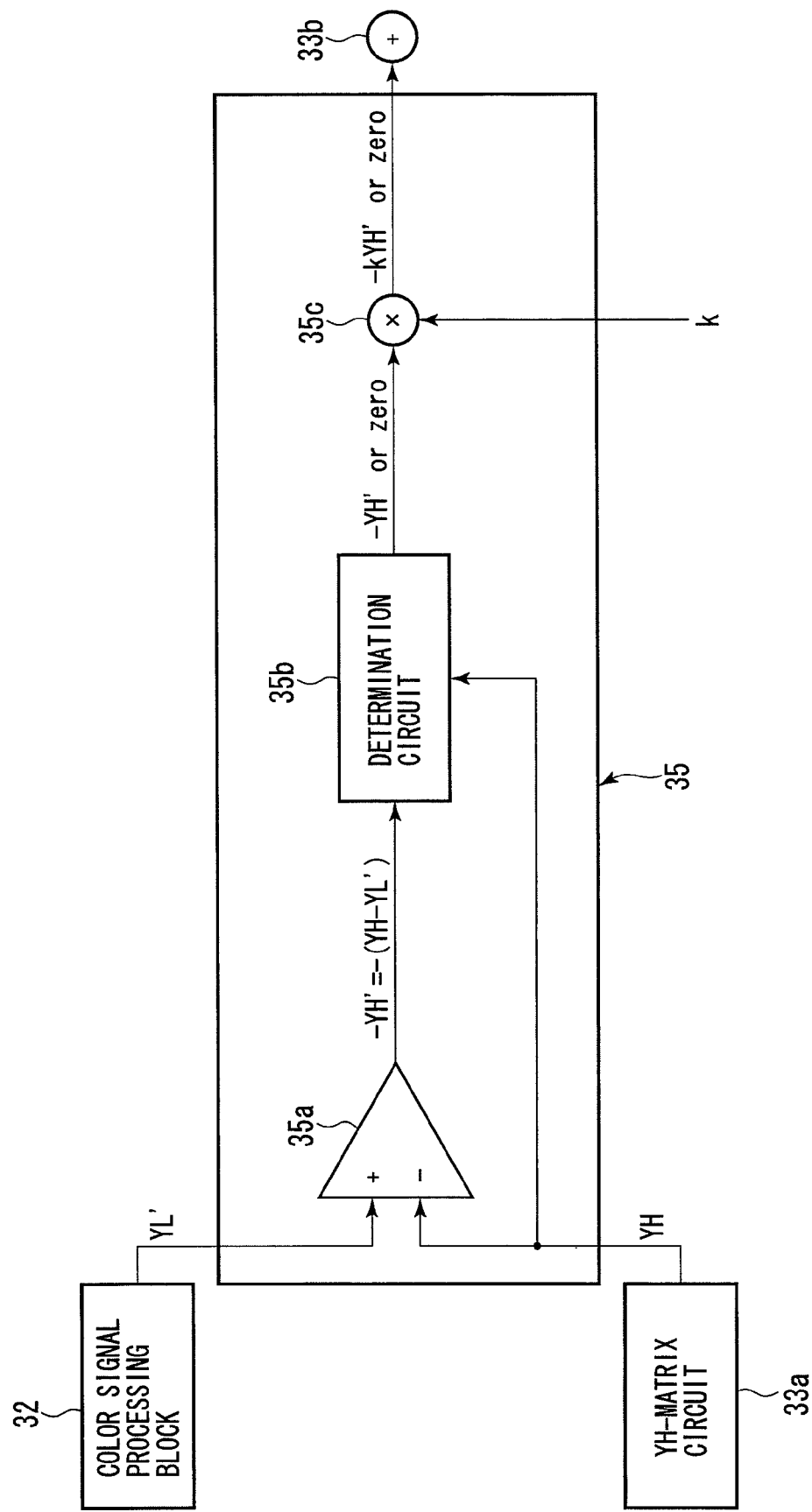
FIG. 8 is a block diagram showing the internal structure of the calculation circuit in the first and second embodiments.

Next, the structure and function of the calculation circuit 35 as it calculates kYH' is explained in detail. As shown in FIG. 8, the calculation circuit 35 comprises a subtractor circuit (second luminance calculation block) 35a, a determination circuit 35b, and a multiplier circuit 35c.

As described above, the calculation circuit 35 receives YH from the YH-matrix circuit 33a and YL' from the color-signal processing block 32. In addition, the calculation circuit 35 receives a predetermined coefficient for multiplying, hereinafter referred to as k, from a ROM (not depicted). k is in the range of zero to one (i.e. 0<k<1). In addition, the signal input to the calculation circuit 35 is controlled so that YH and YL' simultaneously received by the calculation circuit comes from the same pixel 26p.

YH is input to the subtractor circuit 35a and the determination circuit 35b. YL' is input to the subtractor circuit 35a. k is input to the multiplier circuit 35c.

The subtractor circuit 35a generates a second wide-band luminance signal (second luminance), hereinafter referred to as YH', by subtracting YL' from YH. And after negation, YH' is output. Specifically, the subtractor circuit 35a subtracts YH from YL'. After multiplication by −1, YH' is output from the subtractor circuit 35a to the determination circuit 35b.

The determination circuit 35b (the comparison block) compares the YH transmitted from the YH-matrix circuit 33a and a first threshold value. The first threshold value is stored in a ROM (not depicted) and read by the determination circuit 35b for comparison with YH. If YH is greater than the first threshold value, the determination circuit 35b outputs YH' multiplied by −1 to the multiplier circuit 35c. If the first threshold value is greater than YH, the determination circuit 35*b* outputs the zero signal rather than YH' to the multiplier circuit 35*c*.

The multiplier circuit 35*c* multiplies the received signal by k. Accordingly, if the determination circuit 35*b* output YH', the multiplier circuit 35*c* calculates the correction signal, equivalent to kYH'=k(YH−YL'). On the other hand, if the determination circuit 35*b* outputs the zero signal, the signal calculated by the multiplier circuit 35*c* will be the zero signal. Thus, either kYH' multiplied by −1, or the zero signal, is transmitted to the adder circuit 33*b*.

As described above, the adder circuit 33*b* calculates YH" based on YH, and kYH' or the zero signal. YH", having undergone gamma correction processing, is encoded with R-YL and B-YL, and YH", R-YL, and B-YL are transmitted to the endoscope processor 11 as a video signal.

The endoscope processor 11 comprises a memory (not depicted). The memory stores YH", R-YL, and B-YL received by the endoscope processor 11. The YH", the R-YL, and the B-YL stored in the memory are transmitted to the monitor 12. The monitor 12 generates R, G, and B components based on the received YH", R-YL, and B-YL. An image corresponding to the generated primary color signal components is displayed on the monitor 12.

Figure 9:
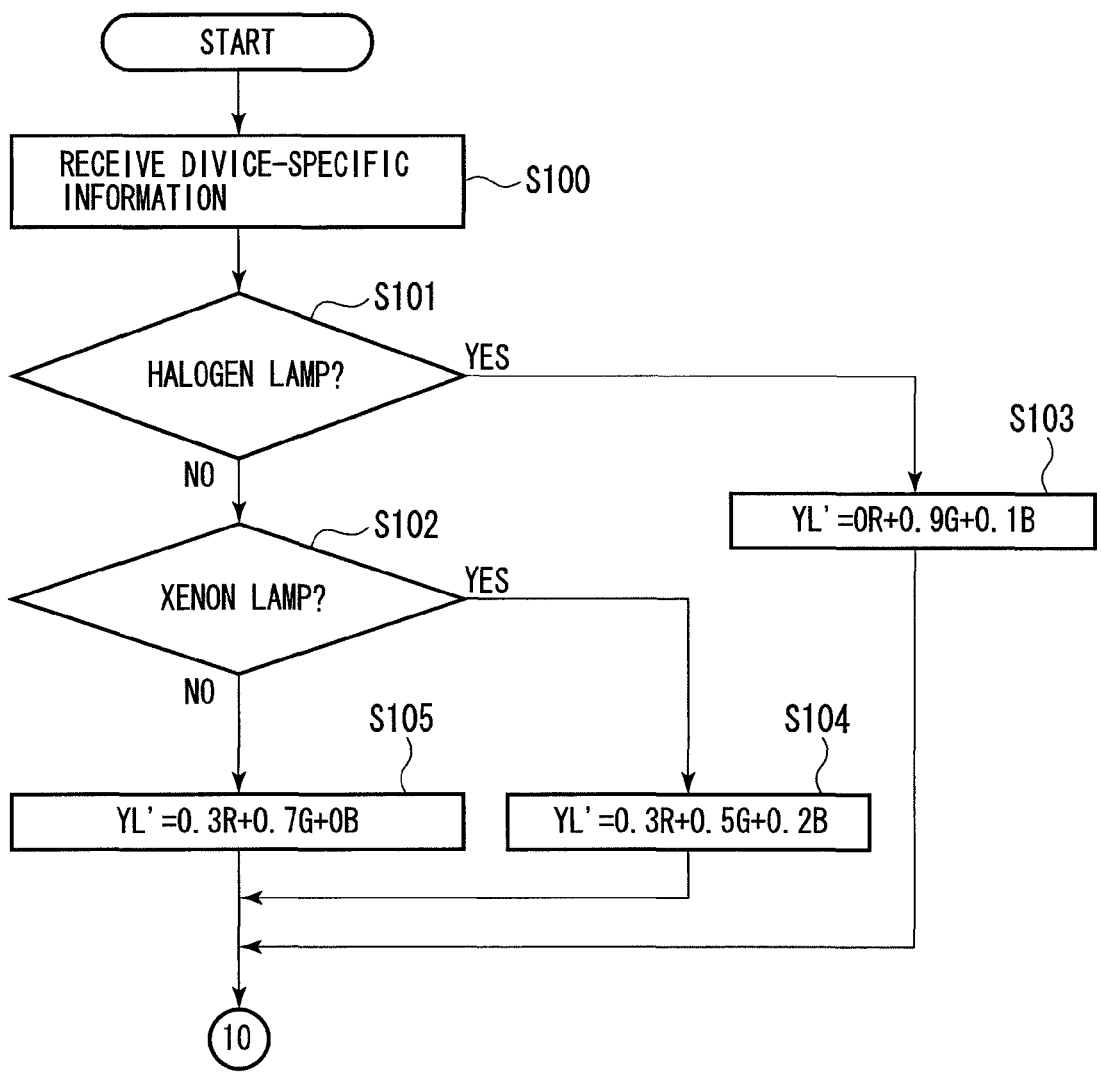
FIG. 9 is a flowchart illustrating the process for calculating the second narrow-band luminance signal in the first embodiment.

Next, the image-signal processing performed by the signal-processing unit 30 in the first embodiment will be explained, using the flowcharts of FIGS. 9 and 10. The processing carried out by the signal-processing unit 30 starts when the electronic endoscope 20 is connected to the endoscope processor 11 and the endoscope processor 11 is switched on. In addition, the processing ends when the operation mode of the endoscope processor 11 is changed to a mode other than the observation mode or the endoscope processor 11 is switched off.

In step S100, the device-specific information is read from the endoscope processor 11. In steps S101 and S102, described below, the kind of light source in the endoscope processor connected to the electronic endoscope 20 is determined based on the read device-specific information.

In step S101, it is determined whether the light source is a halogen lamp. If the light source is determined to be a halogen lamp, the process proceeds to step S103. If it is not, the process proceeds to step S102. In step S102, it is determined whether the light source is a xenon lamp. If the light source is determined to be a xenon lamp, the process proceeds to step S104. If it is not, the light source is determined to be a metal halide lamp and the process proceeds to step S105.

In step S103, YL' is calculated using the coefficients 0, 0.9 and 0.1 for R, G, and B, respectively, for the case of the halogen lamp. In step S104, YL' is calculated using the coefficients 0.3, 0.5 and 0.2 for R, G, and B, respectively, for the case of the xenon lamp. In step S105, YL' is calculated using the coefficients 0.3, 0.7 and 0 for R, G, and B, respectively, for the case of the metal halide lamp.

After calculating YL' in steps S103, S104, or S105, the process proceeds to step S106. At step S106, the mixed pixel signals (Mg+Cy), (G+Ye), (G+Cy), and (Mg+Ye) are received.

In step S107, R-YL, B-YL, and YL' are generated based on the mixed pixel signals (Mg+Cy), (G+Ye), (G+Cy), and (Mg+Ye).

In step S108, YH is generated based on the mixed pixel signals (Mg+Cy), (G+Ye), (G+Cy), and (Mg+Ye). After generating YH, YH' is generated based on YH and YL'.

After calculating YH', the process proceeds to step S110. In step S110, it is determined whether the signal level of YH is greater than the first threshold value. If YH is greater than the first threshold value, the process proceeds to step S111. On the other hand, if YH does not exceed the first threshold value, the process proceeds to step S112.

In step S111, kYH' is calculated using the YH' generated at step S108. On the other hand, in step S112, YH' is discarded and the zero signal is generated instead of YH'.

After calculating kYH' or generating the zero signal, the process proceeds to step S113. In step S113, YH is corrected using kYH' or the zero signal, then YH" is generated.

YH" is output from the signal-processing unit 30 with R-YL and B-YL generated in step S107. After outputting YH", the process returns to step S106, and steps S106-S112 are repeated.

In the first embodiment above, true colors can be displayed in an image based on the image signal independent of the color of the captured optical image. In addition, true colors can be displayed in an image based on the image signal independent of the color of the illumination light. These effects are explained in detail below.

In a general endoscope system, an imaging device is covered with complementary color filters and generates the Mg, Cy, Ye, and G signals, as in the first embodiment. The chrominance difference signals and the luminance signal are generated based on the complementary-color signal components. The generated chrominance difference signal and luminance signal are transmitted to a monitor. The monitor generates primary-color signal components, such as R, G, and B, based on the received chrominance difference signal and luminance signal. Alternatively, an electronic endoscope or an endoscope processor may generate the primary-color signal components based on the chrominance difference signal and the luminance signal, and transmit the primary color signal components to a monitor.

A wide-band luminance signal is used as a luminance signal to generate the primary-color signal components at a monitor in order to reduce the influence of noise. In addition, the chrominance difference signals calculated by subtracting the narrow-band luminance signal from R and B are used to generate the primary color signal components in a monitor in order to display true colors.

The wide-band luminance signal is calculated by summing Mg, Cy, Ye, and G. Accordingly, the wide-band luminance signal is equivalent to 2R+3G+3B. On the other hand, the narrow-band luminance signal is calculated by generating R, G, and B based on Mg, Cy, Ye, and G, and multiplying the R, G, and B by the predetermined coefficients 0.3, 0.59, and 0.11, respectively, and then summing the R, G, and B. Thus, the narrow-band luminance signal is equal to 0.3R+0.59G+0.11B.

The ratio of the coefficient for R to the coefficient for G is 0.67 for the wide-band luminance signal and 0.51 for the narrow-band luminance signal. Accordingly, the effect of R on the wide-band luminance signal is greater than it is on the narrow-band luminance signal. Consequently, if a reddish subject is observed with the endoscope system, the signal level of R generated by adding the wide-band luminance signal to the chrominance difference signal calculated with the narrow-band luminance signal may exceed the upper limit of a digital circuit, even if the signal level of the wide-band luminance signal is below the upper limit of the digital circuit. Usually, the subject observed with a medical electronic endoscope is an internal organ. Thus, since the image of the subject is mostly reddish, it is possible for the signal level of R to exceed the upper limit.

On the other hand, in the endoscope system 10 of the first embodiment, the signal level of kYH' to be subtracted from YH becomes large in proportion to the amount of red light received by a pixel 26p. Consequently, the signal level of YH" becomes small in proportion to the amount of red light received by a pixel 26p. That results in preventing the signal level of R from exceeding the upper limit of a digital circuit even if the amount of red light is large.

In addition, the ratio of the coefficient for B to the coefficient for G in the wide-band luminance signal is greater than it is for the narrow-band luminance signal, as it is for R. Accordingly, the effect of B on the wide-band luminance signal is greater than it is on the narrow-band luminance signal. Consequently, if a bluish subject is observed with the endoscope system, the signal level of B generated by adding the wide-band luminance signal to the chrominance difference signal calculated from the narrow-band luminance signal may exceed the upper limit of a digital circuit, even if the signal level of the wide-band luminance signal is under the upper limit of the digital circuit.

In addition to the above effect, in the first embodiment, a luminance signal for generating primary color signal components can be adequately corrected according to the kind of light source, as described below. Various light sources may be used in an electronic endoscope depending on the subject. The intensities of red and blue light components in the illumination light vary according to the kind of light source. In the first embodiment, the influence of the primary color signal components on the kYH' is adjusted by changing the coefficients used to calculate YL' according to the kind of light source. It is possible to prevent the signal levels of the red and blue light signal components from exceeding the upper limit by controlling the influence of the primary color signal components.

In addition to the above effects, in the first embodiment, the LPF 32f removes the high frequency components from the spatial frequency of the YL'. As explained below, sharp transitions in YH" across space are contrast-enhanced by removing the high frequency components from YL'.

Figure 11:
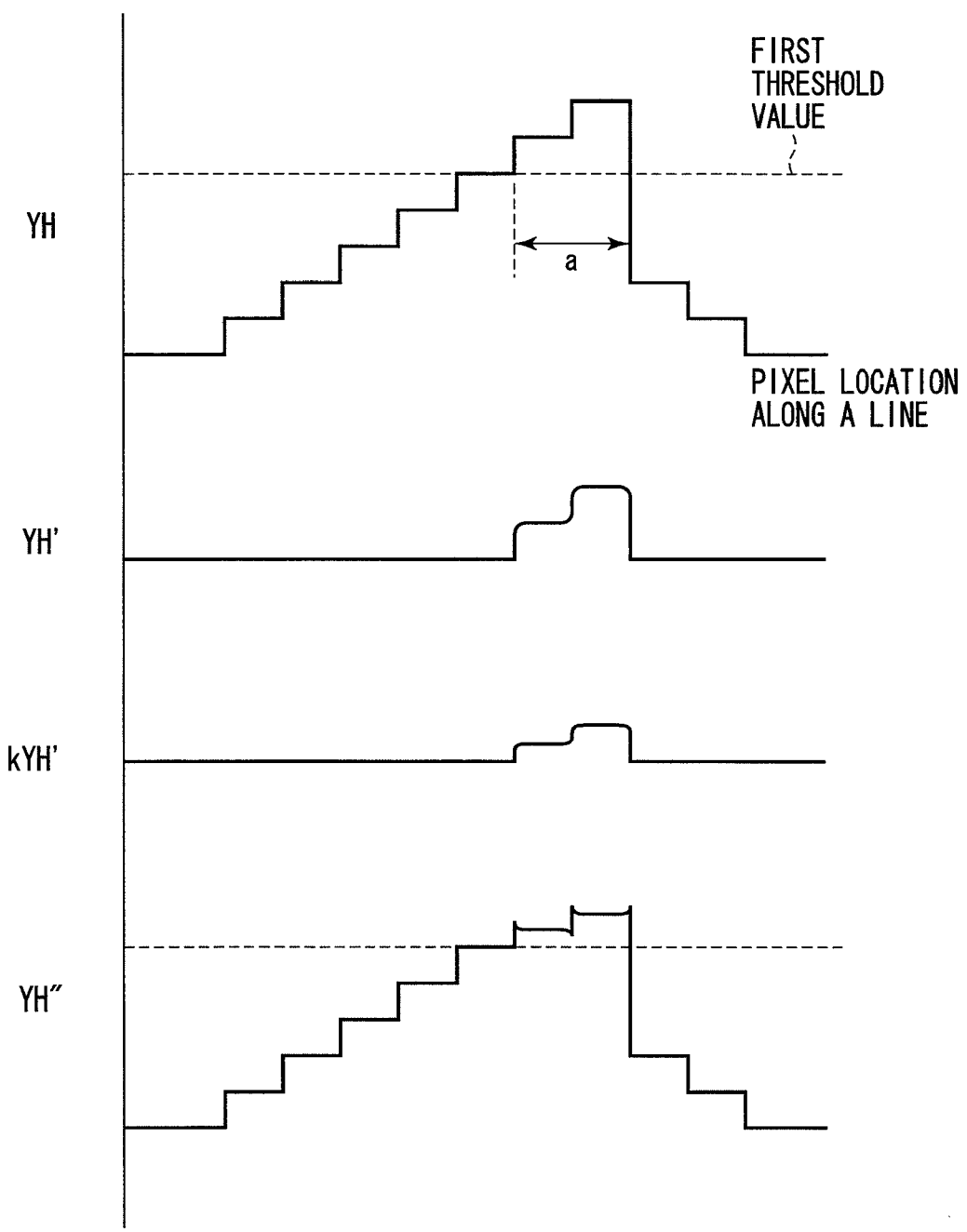
FIG. 11 is a graph showing the luminance signal levels of pixels arranged in line in order to explain the effect of edge enhancement.

For example, the wide-band luminance signal is corrected for pixels where the original wide-band luminance signal exceeds the first threshold value (FIG. 11, see "a" in row "YH"). To correct the wide-band luminance signal there, YH' is calculated by subtracting YL' from YH. By removing the high-frequency components from the spectrum of YL', the high-frequency components of the spectrum of YH' are removed (see row "YH'" in FIG. 11). The signal level is lowered by multiplying YH' by k. Sharp transitions in YH" across space are contrast-enhanced by subtracting kYH' from YH (see row "YH''" in FIG. 11).

In particular, edges in an image based on YH" without edge-enhancement are easily blurred because the rate of change in YH" is lower than that of the actual brightness. Therefore, the technique of edge-enhancement by correction of the luminance signal is implemented in the first embodiment in order to reduce such blurring.

Next, an endoscope system with an image-signal processor of the second embodiment is explained. The primary difference between the second embodiment and the first embodiment is that the signal-processing unit is mounted in an endoscope processor rather than in an electronic endoscope. The second embodiment is explained mainly with reference to the structures that differ from those of the first embodiment. Here, the same index numbers are used for the structures that correspond to those of the first embodiment.

Figure 12:
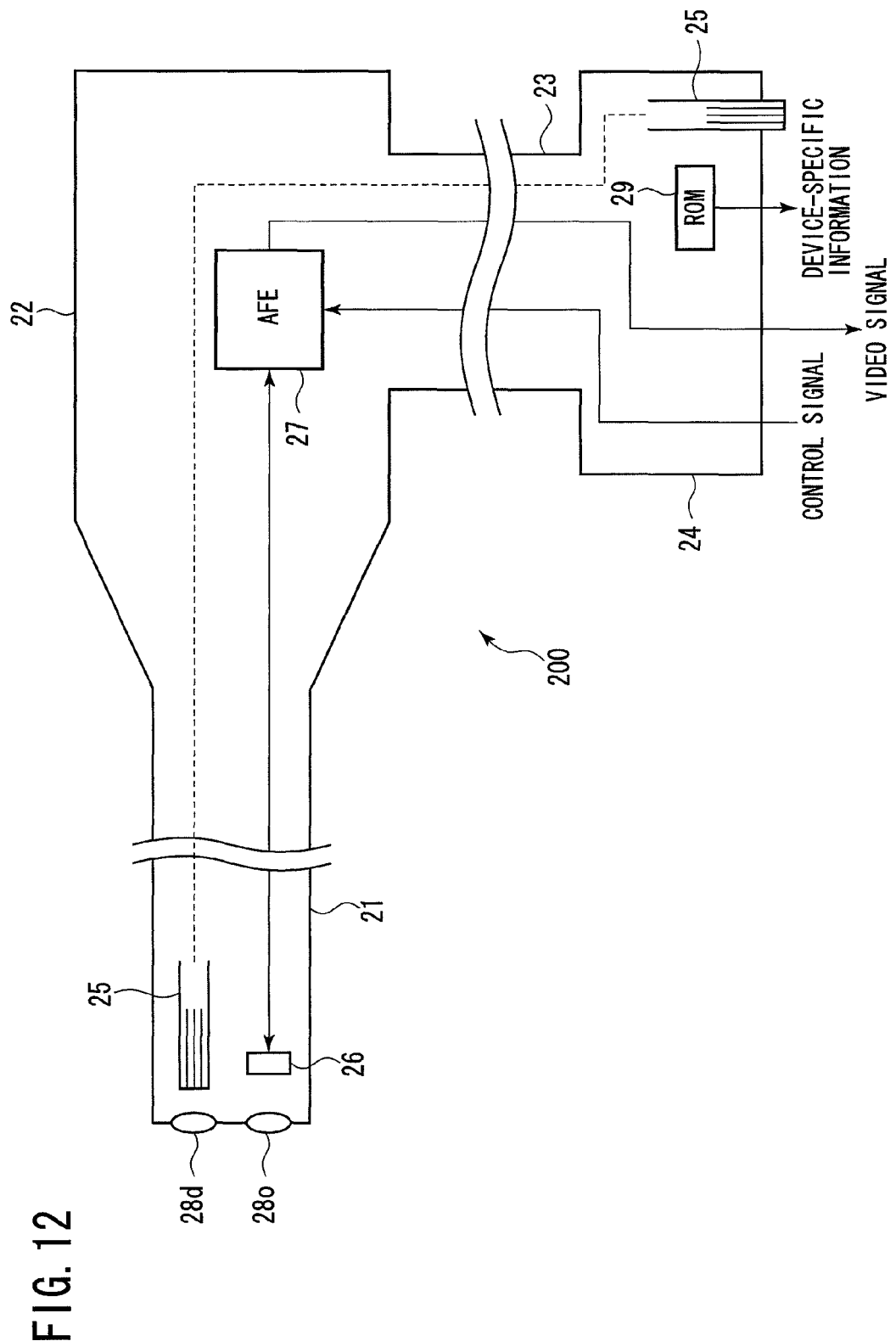
FIG. 12 is a block diagram showing the internal structure of the electronic endoscope of the second embodiment.

As shown in FIG. 12, the electronic endoscope 200 comprises a light guide 25, an imaging device 26, an AFE 27, a ROM 29, and other components. The arrangements and functions of the light guide 25, the imaging device 26, and the AFE 27 are the same as those of the first embodiment.

The ROM 29 is mounted in a connector 24, and stores device-specific information indicating the model type of the electronic endoscope 200. For example, some model types include bronchial endoscopes, upper digestive tract endoscopes, lower digestive tract endoscopes, and so on. When the connector 24 is connected to the endoscope processor 11, the ROM 29 is connected to a signal-processing unit 30 mounted in the endoscope processor 11. The signal-processing unit 30 reads the device-specific information.

In addition, mixed pixel signals (Mg+Cy), (G+Ye), (G+Cy), and (Mg+Ye) output from the AFE 27 are also transmitted to the signal-processing unit 30.

As described above, the signal-processing unit 30 of the second embodiment is mounted in the endoscope processor 11. The structure and function of the signal-processing unit 30 except for the use of coefficients to calculate YL' according to the device-specific information are the same as those of the first embodiment.

As shown in FIG. 4, the signal-processing unit 30 of the second embodiment also comprises an AGC 31, a color-signal processing block 32, a luminance-signal processing block 33, and an encoder 34. The signal-processing unit 30 generates the YH", the R-YL, and the B-YL, just as in the first embodiment. In addition, the signal-processing unit 30 generates a video signal based on YH", R-YL, and B-YL. The video signal is transmitted to the monitor 12.

Figure 13:
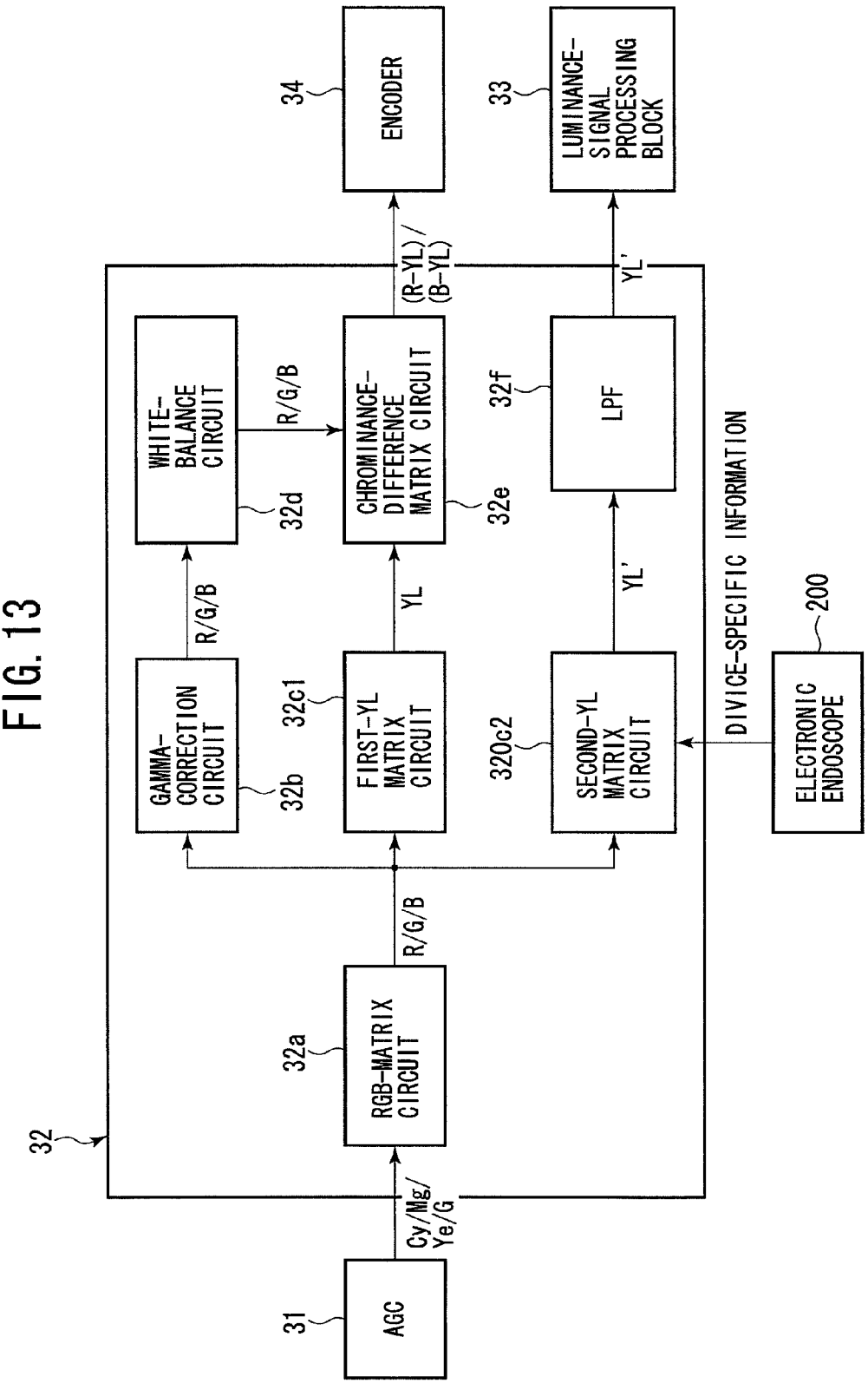
FIG. 13 is a block diagram showing the internal structure of the color-signal processing block in the second embodiment.

As shown in FIG. 13, the color-signal processing block 32 of the second embodiment comprises an RGB-matrix circuit 32a, a gamma-correction circuit 32b, first- and second-YL matrix circuits 32c1 and 320c2, a white-balance circuit 32d, a chrominance-difference matrix circuit 32e, and an LPF 32f. The device-specific information transmitted to the second-YL matrix circuit (endoscope determination block) 320c2 which the signal-processing unit 30 comprises differs from that of the first embodiment.

The arrangement and the structure of the RGB-matrix circuit 32a, the gamma-correction circuit 32b, the first-YL matrix circuit 32c1, the white-balance circuit 32d, the chrominance-difference matrix circuit 32e, and the LPF 32f are the same as those of the first embodiment.

The second-YL matrix circuit 320c2 is connected to the ROM 29 mounted in the electronic endoscope 200, unlike in the first embodiment. The device-specific information, which indicates the model type of the connected electronic endoscope, is transmitted from the ROM 29 to the second-YL matrix circuit 320c2.

The second-YL matrix circuit 320c2 generates the YL' by summing the R, G, and B, multiplied by coefficients predetermined according to the device-specific information, just as in the first embodiment.

If the electronic endoscope 200 is a bronchial endoscope, YL' is calculated as YL'=0.3R+0.5G+0.2B. If the electronic endoscope 200 is an upper digestive tract endoscope, YL' is calculated as YL'=0R+0.9G+0.1B. If the electronic endoscope 200 is a lower digestive tract endoscope, YL' is calculated as YL'=0.3R+0.7G+0B.

The bronchus generally looks pale, and the reflected red light component is small. Consequently, it is necessary to lower the influence of G on the luminance signal. This can be accomplished by lowering the coefficient for G in the equation used to calculate YL'.

The upper digestive tract generally looks reddish. Accordingly, it is necessary to lower the influence of R on the luminance signal. This can be accomplished by lowering the coefficient for R in the equation used to calculate YL'.

The lower digestive tract generally looks bluish. Accordingly, it is necessary to lower the influence of B on the luminance signal. This can be accomplished by lowering the coefficient for B in the equation used to calculate the YL'.

Figure 10:
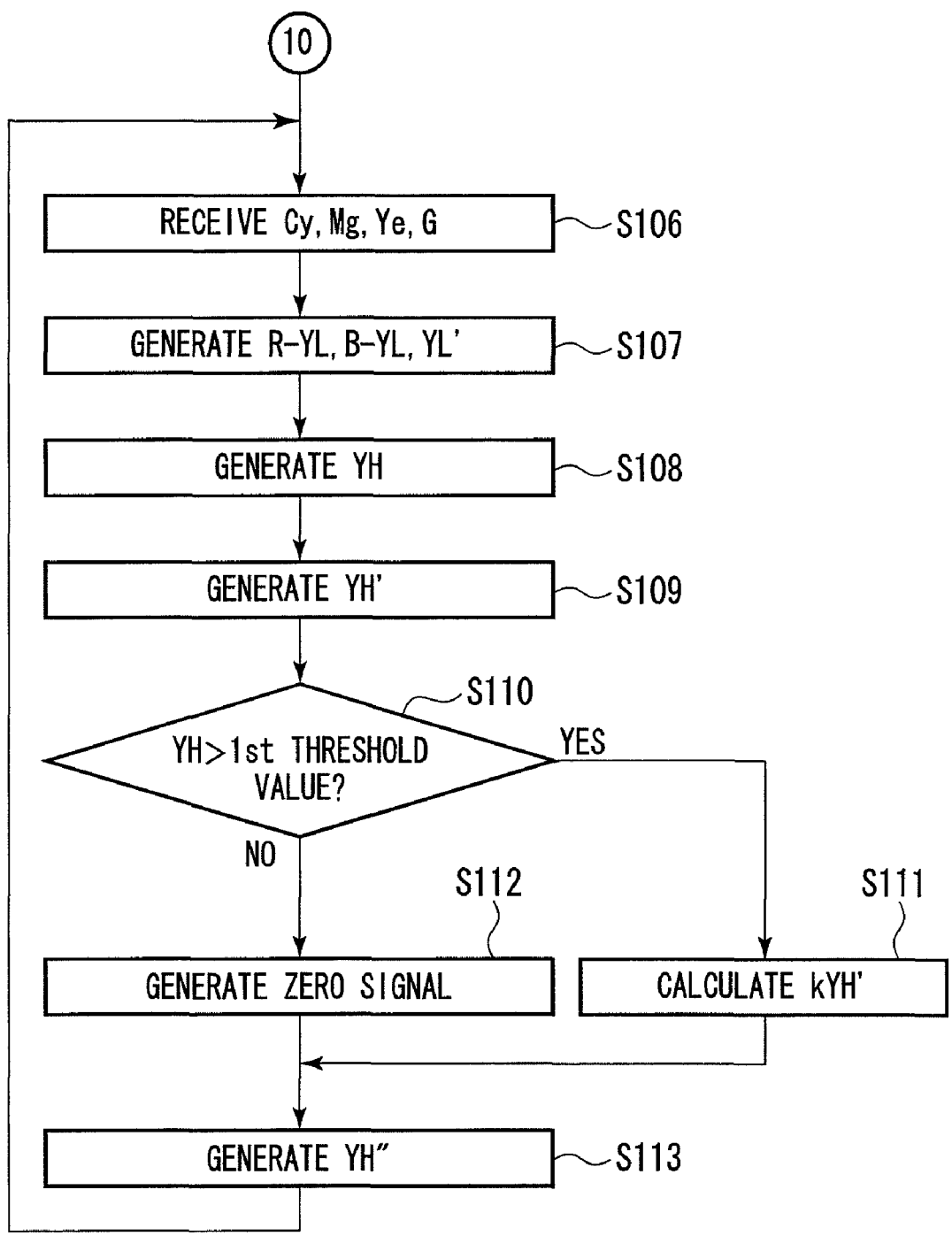
FIG. 10 is a flowchart illustrating the process for generating the corrected luminance signal based on the second narrow-band luminance signal in the first and second embodiments.
Figure 14:
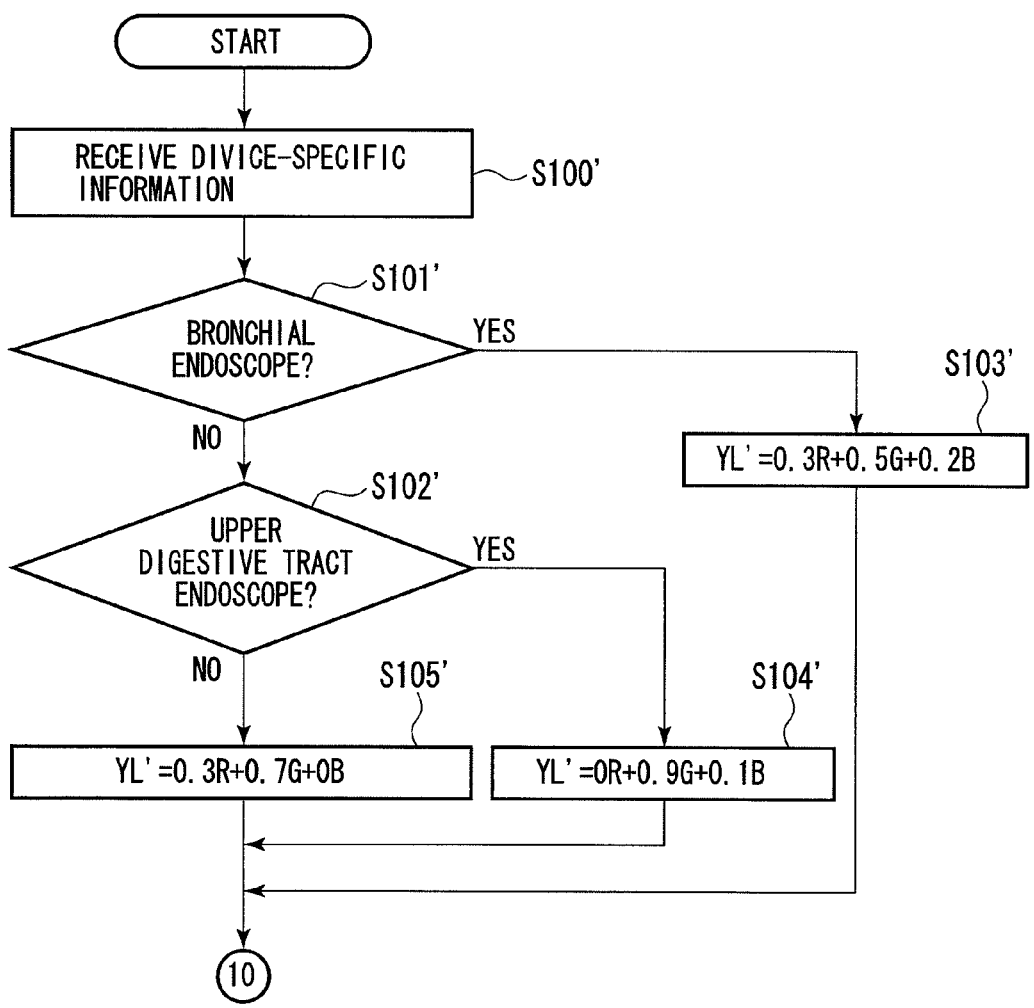
FIG. 14 is a flowchart illustrating the process for calculating the second narrow-band luminance signal in the second embodiment.

Next, the image-signal processing performed by the signal-processing unit 30 in the second embodiment is explained, using the flowcharts of FIGS. 10 and 14. The processing carried out by the signal-processing unit 30 starts when the electronic endoscope 200 is connected to the endoscope processor 11 and the endoscope processor 11 is switched on, as in the first embodiment. In addition, the processing ends when the operation mode of the endoscope processor 11 is changed to a mode other than the observation mode, or the endoscope processor 11 is switched off, as in the first embodiment.

In step S100' (see FIG. 14), the device-specific information is read from the electronic endoscope 200. In steps S101' and S102', described below, the model type of the electronic endoscope 200 connected to the endoscope processor 11 is read from the device-specific information.

In step S101', it is determined whether the electronic endoscope 200 is a bronchial endoscope. If the electronic endoscope 200 is determined to be a bronchial endoscope, the process proceeds to step S103', otherwise the process proceeds to step S102'. In step S102', it is determined whether the electronic endoscope 200 is an upper digestive tract endoscope. If the electronic endoscope 200 is determined to be an upper digestive tract endoscope, the process proceeds to step S104', otherwise the electronic endoscope is determined to be a lower digestive tract endoscope and the process proceeds to step S105'.

In step S103', YL' is calculated using coefficients 0.3, 0.5 and 0.2 for R, G, and B, respectively, for the case of a bronchial endoscope. In step S104', YL' is calculated with coefficients 0, 0.9 and 0.1 for R, G, and B, respectively, for the case of an upper digestive tract endoscope. In step S105', YL' is calculated with coefficients 0.3, 0.7 and 0 for R, G, and B, respectively, for the case of a lower digestive tract endoscope.

After calculating YL' in steps S103', S104', or S105', the process proceeds to step S106 (see FIG. 10). Then steps S106-S113 are carried out, as in the first embodiment.

In the second embodiment, true colors can also be displayed in an image based on the image signal independent of the coloration of the image, as in the first embodiment. In addition, true colors can be displayed in an image based on the image signal independent on the subject observed with the electronic endoscope connected to the endoscope processor.

In the first and second embodiments, YH' is calculated by subtracting YL', generated by the second-YL matrix circuit 32c2 or 320c2 based on R, G, and B, from YH. However, the second-YL matrix circuit 32c2 or 320c2 directly generates YH' by summing the R, G, and B multiplied by predetermined coefficients (the second coefficient combination), and the generated YH' can be used for the YH" calculation. In that case, the ratio of the coefficient for R to the coefficient for G in the YH' calculation should be set larger than the ratio of the coefficient for R to the coefficient for G in the YH calculation.

By determining the coefficient for R in the YH' calculation according to the condition above, the effect of R on YH" can be reduced. In order to reduce the effect of B on YH", the ratio of the coefficient for B to the coefficient for G in the YH' calculation should be set larger than the ratio of the coefficient for B to the coefficient for G in the YH calculation.

In the first and second embodiments, the signal-processing unit 30 generates and outputs a video signal based on R-Yl, B-YL, and YH". However, the signal-processing unit 30 may instead generate R, G, and B in an RGB generation circuit (color-signal generation block) based on the pre-generated R-YL, B-YL, and YH", and output the R, G, and B to an external apparatus.

In the first and second embodiments, the pixels 26p are covered with complementary-color filters. However, they may instead be covered with primary-color filters of red, green, and blue. In this case, the generated pixel signals would be R, G, and B signals, which vary according to the amount of red, green and blue light received. Accordingly, in order to carry out the signal processing of the first and second embodiments, complementary-color signal components Mg, Cy, Ye, and G would need to be generated by a complementary-color signal generation circuit (not depicted) based on the R, G, and B, whereupon the Mg, Cy, Ye, and G could undergo signal processing. Alternatively, the YH, YL, and YL' may be generated by summing the R, G, and B multiplied by their respective predetermined coefficients.

In the first and second embodiments, high-frequency components exceeding a predetermined frequency are removed by the single LPF 32f. However, the cut-off frequency may be selected by using a plurality of LPFs, each with a different cut-off frequency. It is thus possible to change the sharpness of an edge in the displayed image by changing the cut-off frequency.

For example, the cut-off frequency can be automatically adjusted according to the signal level of the YH. First and second threshold values, the first threshold value being greater than the second threshold value, are predetermined for comparison with YH at the determination circuit 35b. When the signal level of YH exceeds the first threshold value, the cut-off frequency may be changed from that when the signal level of YH is between the first and the second threshold values.

In addition, even if the LPF is not mounted in the first or second embodiments, true colors may also be displayed in an image independent of the color of the captured subject.

In the first and second embodiments, the first threshold value is fixed. However, the first threshold value may be changeable. The first threshold value could be manually changed by a user or automatically changed by an apparatus of the endoscope processor 10.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2007-013038 (filed on Jan. 23, 2007), which is expressly incorporated herein, by reference, in its entirety.

The invention claimed is:

1. An image-signal processing unit comprising:
a receiver that receives an image signal, said image signal comprising a plurality of pixel signals, each pixel signal being generated according to an amount of light received by a pixel, a plurality of pixels being arranged on a light-receiving surface of an imaging device;
a first luminance calculator that calculates a first luminance corresponding to the sum of a plurality of primary color light components, each multiplied by a coefficient from a first coefficient combination, for each of said pixels, based on said image signal, the first luminance being a wide band luminance signal calculated based upon color signal components corresponding to complementary color filter elements Mg, Cy, Ye and G;
a second luminance calculator that calculates a second luminance corresponding to the sum of a plurality of said primary color light components, each multiplied by a coefficient from a second coefficient combination, for each of said pixels, based on said image signal, wherein a ratio of the coefficient by which a first primary color light component is multiplied, to the coefficient by which a second primary color light component is multiplied, is greater than the ratio in said first coefficient combination, the second luminance being a narrow band luminance signal calculated based upon primary color signals R, G, and B the primary color signals being calculated based upon color signal components corresponding to the complementary color filter elements;

a comparator that compares said first luminance with a threshold value;

a correction-value calculator that calculates a luminance correction value according to said second luminance when said first luminance is greater than said threshold value; and a subtractor that calculates a corrected luminance by subtracting said luminance correction value from said first luminance.

2. An image-signal processing unit according to claim 1, further comprising:

a chrominance-difference calculator that calculates a chrominance difference for each of said pixels, based on said image signal; and an outputter that outputs a chrominance difference signal and a luminance signal, corresponding to said chrominance difference and said corrected luminance, respectively, for each of said pixels, when said first luminance is greater than said threshold value; and outputs a chrominance difference signal and a luminance signal, corresponding to said chrominance difference and said first luminance, respectively, for each of said pixels, when said first luminance is lower than said threshold value.

3. An image-signal processing unit according to claim 1, further comprising:

a chrominance-difference calculator that calculates a chrominance difference for each of said pixels, based on said image signal; and a color-signal generator that generates primary-color signal components corresponding to said primary-color light components, for each of said pixels, based on said chrominance difference and said corrected luminance when said first luminance is greater than said threshold value; and generates primary-color signal components corresponding to said primary color light components, for each of said pixels, based on said chrominance difference and said first luminance when said first luminance is lower than said threshold value.

4. An image-signal processing unit according to claim 1, wherein said second coefficient combination is changeable.

5. An image-signal processing unit according to claim 4, further comprising a light-source determiner that determines a kind of light source emitting illumination light for a subject, an optical image of the subject being captured by said imaging device, and said second coefficient combination being modified according to the determination of the kind of light source by said light-source determiner, said image-signal processing unit being mounted in an endo scope comprising said imaging device.

6. An image-signal processing unit according to claim 4, further comprising an endoscope determiner that determines a kind of endo scope comprising said imaging device, the second coefficient combination being modified according to the determination of the kind of endoscope made by said endoscope determiner, said image-signal processing unit being mounted in an endoscope processor that carries out signal processing on said image signal.

7. An image-signal processing unit according to claim 1, further comprising an edge-enhancer that enhances edges in an image based on said corrected luminance.

8. An image-signal processing unit according to claim 7, wherein the sharpness of said edges enhanced by said edge-enhancer is adjustable.

9. An image-signal processing unit according to claim 8, wherein first and second threshold values are predetermined as said threshold value, said second threshold value being lower than said first threshold value, and said edge-enhancer modifies said sharpness according to whether said first luminance is between said first and second threshold values or said first luminance exceeds said first threshold value.

10. An image-signal processing unit according to claim 1, wherein said threshold value is adjustable.

11. An image-signal processing unit according to claim 1, wherein said luminance correction value is calculated by multiplying said second luminance by a predetermined coefficient lower than one.

12. An image-signal processing unit according to claim 1, further comprising a third luminance calculator that calculates a third luminance corresponding to the sum of a plurality of said primary-color light components, each multiplied by a coefficient from a third coefficient combination, for each of said pixels, based on said image signal, wherein the ratio of the coefficient by which a first primary-color light component is multiplied, to the coefficient by which a second primary-color light component is multiplied, is lower than the ratio in said first coefficient combination, said second luminance calculator calculating said second luminance by subtracting said third luminance from said first luminance.

13. An image-signal processing unit according to claim 12, wherein, said image signal comprises complementary-color signal components, said first luminance calculator calculates said first luminance by adding a plurality of said complementary-color signal components for each of said pixel signals, and said third luminance calculator calculates a plurality of primary-color signal components based on a plurality of said complementary color signal components for each of said pixels, said third luminance calculator multiplying a plurality of said primary color signal components by said third coefficient combination.

14. An image-signal processing unit according to claim 12, further comprising a complementary-color signal generator that generates said complementary-color signal components based on primary-color signal components, said image signal comprising said primary-color signal components, said first luminance calculator calculating said first luminance by adding a plurality of said complementary-color signal components for each of said pixels, and said third luminance calculator multiplying a plurality of said primary color signal components by said third coefficient for each of said pixels.

15. An image-signal processing unit according to claim 12, wherein, said image signal comprises primary-color signal components, said first luminance calculator multiplies a plurality of said primary color signal components by said first coefficient combination for each of said pixels, and said third luminance calculator multiplies a plurality of said primary-color signal components by said third coefficient combination for each of said pixels.

16. An image-signal processing unit comprising:

a receiver that receives an image signal from an imaging device, said imaging device comprising a plurality of pixels on a light-receiving surface, each of said pixels being covered with one of four color filters, said four color filters each passing one of four different complementary colors, said pixels generating a complementary color signal component according to the amount of light passing through said covering color filter, said image signal comprising a plurality of said complementary color signal components;

a first luminance calculator that calculates wide-band luminance by summing four of said complementary color signal components corresponding to said four different complementary colors, the first luminance being a wide band luminance signal calculated based upon color signal components corresponding to complementary color filter elements Mg, Cy, Ye and G;

a primary-color signal generator that generates primary color signal components of three primary colors based on said complementary color signal components;

an other luminance calculator that calculates narrow-band luminance by summing three of said primary color signal components, each multiplied by a coefficient from an other coefficient combination, for each of said pixels, based on said image signal, wherein a ratio of the coefficient by which the first primary color signal component is multiplied, to the coefficient by which the second primary color signal component is multiplied, is lower than the ratio in the first coefficient combination, said wide-band luminance corresponding to the sum of a plurality of primary color signal components, each multiplied by a coefficient from said first coefficient combination;

a comparator that compares said wide-band luminance with a threshold value; and a luminance-signal corrector that calculates a corrected luminance by subtracting said narrow-band luminance multiplied by a multiplying coefficient from said wide-band luminance when said wide-band luminance is greater than said threshold value, said multiplying coefficient being a predetermined value between zero and one.

17. An image signal processing unit comprising:

a receiver that receives an image signal, said image signal comprising a plurality of pixel signals, each pixel signal being generated according to an amount of light received by a pixel, a plurality of pixels being arranged on a light receiving surface of an imaging device;

a first luminance calculator that calculates a first luminance corresponding to the sum of a plurality of primary color light components, each multiplied by a coefficient from a first coefficient combination, for each of said pixels, based on said image signal, the first luminance being a wide band luminance signal calculated based upon color signal components corresponding to complementary color filter elements Mg, Cy, Ye and G;

a second luminance calculator that calculates a second luminance corresponding to the sum of a plurality of said primary color light components, each multiplied by a coefficient from a second coefficient combination, for each of said pixels, based on said image signal, wherein a ratio of the coefficient by which a first primary color light component is multiplied, to the coefficient by which a second primary color light component is multiplied, is greater than the ratio in said first coefficient combination, the second luminance being a narrow band luminance signal calculated based upon primary color signals R, G, and B, the primary color signals being calculated based upon color signal components corresponding to the complementary color filter elements;

a third luminance calculator that calculates a third luminance corresponding to the sum of a plurality of said primary color light components, each multiplied by a coefficient from a third coefficient combination, for each of said pixels, based on said image signal, wherein a ratio of the coefficient by which a first primary color light component is multiplied, to the coefficient by which a second primary color light component is multiplied, is lower than a ratio in said first coefficient combination, said second luminance calculator calculating said second luminance by subtracting said third luminance from said first luminance;

a comparator that compares said first luminance with a threshold value;

a correction value calculator that calculates a luminance correction value according to said second luminance when said first luminance is greater then said threshold value; and a subtractor that calculates a corrected luminance by subtracting said luminance correction value from said first luminance.

18. The image signal processing unit according to claim 17, wherein said image signal comprises complementary color signal components, said first luminance calculator calculates said first luminance by adding a plurality of said complementary color signal components for each of said pixel signals, and said third luminance calculator calculates a plurality of primary color signal components based on a plurality of said complementary color signal components for each of said pixels, said third luminance calculator multiplying a plurality of said primary color signal components by said third coefficient combination.

19. The image signal processing unit according to claim 17, further comprising a complementary color signal generator that generates said complementary color signal components based on primary color signal components, said image signal comprising said primary color signal components, said first luminance calculator calculating said first luminance by adding a plurality of said complementary color signal components for each of said pixels, and said third luminance calculator multiplying a plurality of said primary color signal components by said third coefficient for each of said pixels.

20. The image signal processing unit according to claim 17, wherein said image signal comprises primary color signal components, said first luminance calculator multiplies a plurality of said primary color signal components by said first coefficient combination for each of said pixels, and said third luminance calculator multiplies a plurality of said primary color signal components by said third coefficient combination for each of said pixels.

* * * * *